United States Patent [19]

Shields

[11] Patent Number: 5,401,249
[45] Date of Patent: Mar. 28, 1995

[54] SAFELY DISPOSABLE, NON-REUSABLE INJECTION DEVICE

[76] Inventor: Jack W. Shields, 1950 Las Tunas Rd., Santa Barbara, Calif. 93103

[21] Appl. No.: 73,338
[22] Filed: Jun. 7, 1993
[51] Int. Cl.⁶ ............................................. A61M 5/00
[52] U.S. Cl. .................... 604/187; 604/195; 604/110
[58] Field of Search ............... 604/187, 110, 192, 197, 604/198, 218, 263, 168, 199, 195, 194; 128/919

[56] References Cited

U.S. PATENT DOCUMENTS

| | | | |
|---|---|---|---|
| 4,826,484 | 5/1989 | Haber et al. | 604/110 |
| 4,826,489 | 5/1989 | Haber et al. | 604/195 |
| 4,842,586 | 6/1989 | Hogan | 604/192 |
| 4,888,002 | 12/1989 | Braginetz et al. | 604/195 |
| 5,007,903 | 4/1991 | Ellard | 604/195 |
| 5,215,536 | 6/1993 | Lampropoulos et al. | 604/220 |
| 5,242,400 | 9/1993 | Blake, III et al. | 604/110 |
| 5,242,419 | 9/1993 | Kiner et al. | 604/195 |
| 5,267,977 | 12/1993 | Feeney, Jr. | 604/198 |
| 5,318,536 | 6/1994 | Williams | 604/110 |

*Primary Examiner*—C. Fred Rosenbaum
*Assistant Examiner*—V. Alexander

[57] ABSTRACT

A syringe/needle combination comprising a leading tightly capped needle with a flanged conical hub; a hollow cylindroid with a leading interior cone slip-connecting to outside cone of the needle hub and containing an inside left hand-threaded Luer-Lok attachable to needle hub flanges, a cylindric body containing an elastomeric piston and a trailing end having inside and outside annular flanges; and a plunger with leading right-handed threads reversibly mating with right-handed threads inside the needle hub, a leading body passing through and securing the elastomeric piston, a trailing body separable from the leading body by breakage or right-hand threaded attachment, and a trailing end with a thumb-piece. If pre-filled with liquid medication, the user screws the trailing part of the plunger to the leading part, removes the needle cap, sticks the patient, empties the hollow cylindroid via the plunger-activated piston, advances and rotates the plunger thumb-piece clockwise to engage the needle hub, retracts the needle-linked plunger until the trailing end of the elastomeric piston is stopped by the trailing inside flange within the hollow cylindroid, breaks or screws off the trailing part of the plunger, and plugs the empty leading cone of the hollow cylindroid with the needle cap reversed.

4 Claims, 2 Drawing Sheets

SAFELY DISPOSABLE, NON-REUSABLE INJECTION DEVICE

FIELD OF THE INVENTION

This invention relates to the prevention of blood-borne diseases transmitted by means of accidental hollow-bore needle sticks in health care workers, as well as transmitted by shared needles reused for injecting intravenous drugs in addicts.

PRIOR ART

The pandemic spread of blood-borne diseases during the last 10 years, especially diseases caused by AIDS or hepatitis viruses, make it imperative to prevent the reuse of needles and syringes by intravenous drug abusers, and to protect health care workers from accidental needle sticks contaminated with infected blood during and after use.

To prevent the reuse of disposable syringes with attachable needles used for injecting non-prescribed drugs, a variety of syringe/needle combinations have been devised. Such devices include means for blunting or bending the tip of a leading hollow-bore steel needle after use; occluding the bore of the needle such that it can not be used again; occluding the bore of the needle with a blunt member which slides through; or making the syringe seize or leak such that the piston becomes useless. Exemplary among these are U.S. Pat. Nos. 3,008,570; 3,107,785; 3,895,633; 3,306,291; 4,300,678; 4,356,822; 4,425,120; 4,639,249; 4,655,751; 4,664,654; 4,666,435; 4,702,738; 4,702,738; 4,702,739; 4,801,295; 4,816,022; and 4,840,619. Other designs employing retractable needles, such as U.S. Pat. Nos. 3,306,290; 4,392,859; and 4,790,822 are on record. Few of these provide means for securely holding retractable hollow-bore steel needles for injecting fluid medications before, as well as after use (Cf. U.S. Pat. Nos. 4,838,863; 4,950,241; 4,978,343; 5,019,044; 5,064,419; 5,176,639).

To protect health care workers obliged to use syringes and needles for injecting prescribed medications into potentially infected patients, safety measures include providing an external separate system for safely trapping and disposing of the needle after use; resheathing an exposed needle by means of permanently locking puncture-resistant tube which slides over the syringe and attached needle; using an automatic spring-like mechanism to extend a protective cap over the sharp tip of the needle; using pneumatic compression to shoot medications without needles; or using blunt cannulae, instead of hollow-bore steel needles to transfer fluids intended for injection. Because the instant invention differs structurally, as well as functionally from all the former, only fundamentals of the pertinent prior art will be reviewed here.

First, the use of an external Luer-Lok on the leading end of a disposable syringe is well known in prior art. The Vacutainer TM holder contains inside threads in the leading end to hold mating outside threads on a double-ended Vacutainer TM needle. The Tubex ® syringe has inside threads in the leading end which match outside threads on the leading end of an inserted glass cartridge with a permanently attached needle. In the case of the standard Luer-Lok syringe, the Vacutainer TM holder and the Tubex ® syringe, the torque necessary for screwing in the needle hub is manually applied outside of the syringe cavity and conventionally right-handed. In the instant invention, a Luer-Lok or threaded female connector with left-handed threads is molded inside the leading end of a disposable syringe or a prefilled cartridge for stabilizing and releasably holding the hub of a hollow-bore steel needle which is inserted from the trailing open end and, therefore, must be torqued counterclockwise into a securely locked position with special instruments inserted through the trailing opening in a standard disposable syringe or a prefilled cartridge.

Second, use of an attached elastomeric piston on the leading end of an inserted plunger used for aspirating fluid into or expelling fluid from a syringe or a cartridge is well known throughout the art. Use of a hollow elastomeric piston attached around the body of a plunger is novel. However, gaskets for making sliding hollow plungers within syringes water-tight have been described in the prior art (Cf. U.S. Pat. Nos. 5,180,369 and 5,180,370).

Third, the use of an inserted plunger whose leading tip releasably attaches to an elastomeric piston by means of a harpoon is common in dental syringes used for expelling the contents of inserted cartridges. Tubex ® medical syringes use threaded connectors on the leading ends of solid plungers to mate with receptive counterparts on elastomeric cartridge pistons to control piston displacement. In such syringes, the leading ends of the pistons or plungers never attach directly to the needle hubs.

Other features not immune to modification in currently standard syringes and needles deserve additional comment:

1. Standard disposable Luer-Lok syringes usually have a constriction in the trailing bore which impedes retraction of an elastomeric piston attached to the leading end of a syringe plunger. This constriction does not, necessarily, constitute a flange or a wedge.
2. Standard elastomeric syringe pistons are customarily made with leading and trailing flanges such that they can be introduced easily through said constriction in the trailing bore of the syringe, as well as reduce friction when sliding back and forth inside under the impetus of a trailing syringe plunger.
3. Standard needle hubs customarily attach to the outside of leading ends of syringes by means of a slip connection which lacks threads, or a Luer-Lok connection wherein a central slip connection is reinforced by a threaded collar which grasps an ovoid flange on the trailing end of the needle hub.
4. Standard ovoid needle hub flanges customarily measure 7.7 mm. in diameter at the apogees, or points farthest from center. At the perigees, or points closest to center, standard ovoid hub flanges customarily measure 6.7 mm. in diameter. Customarily, the threaded collar of the Luer-Lok is coned slightly, such that the perigees of the flange bind to the threads with ±180° clockwise rotation of the needle or the syringe. As results, the slip connection the leading end of the syringe forms a secure and water-tight connection with the tailing conical internal portion of the needle hub.

In U.S. Pat. No. 5,007,901 (Apr. 16, 1991) Shields taught the use of a break-away slip connection on the leading end of a connecting member designed to retract the hub of a catheter insertion needle into a trailing tubular puncture-resistant trap of sufficient length to safely accommodate the leading end of a retracted hollow-bore catheter insertion needle following insertion of a hubbed catheter. Use of a breakable plunger for retracting an activating piston, along with the hub, shaft and tip of a hollow-bore steel needle into a conventional disposable syringe or medication-filled cartridge was not taught.

The concept of inserting a prefilled cartridge with a trailing slotted flange and a permanently attached needle inside the barrel of breech-loading syringe having a sliding plunger for activating the cartridge piston, so that the spent cartridge could be safely breech-ejected by means of leading scabbards was taught by Shields in U.S. Pat. No. 5,176,178 (Jan. 05, 1993).

The concept of retracting a leading cannula or needle by means of a reciprocal plunger into the confines of a syringe was taught in U.S. Pat. No. 4,026,287 (May 31, 1977) by Hailer-Irene. This system depends on making the leading end of the syringe breakable, such that after syringe use, traction on a plunger matingly engagable to the cannula hub fractures the leading part of the syringe to allow internal displacement of the cannula. This concept remains to become useful, possibly because fragility in the leading part of the syringe can result in unacceptable needle stability or leakage during introduction and use.

Recognizing the desirability of retracting a used needle into the puncture-resistant confines of a single use syringe, Nacci & Tagliaferri in U.S. Pat. No. 5,176,640 issued Jan 5, 1993, described a syringe wherein a hollow travelling plunger connects to the hypodermic needle and to a pneumatic activator, preferably of vacuum type, arranged to cause the needle to slide into an appropriate chamber in the plunger after use. This concept has not proven practical, possibly because of complexity; and partly because vacuum in the confines of the plunger requires prolonged maintenance.

Recognizing the medical potential for making a self destructive safety syringe assembly having a needle cannula fixed to a sliding piston, Dyarz in U.S. Pat. No. 5,180,369 (issued Jan. 19, 1993), taught the use of a hollow syringe plunger capable of internally retracting a hollow-bore steel needle by means of an extended hub within the cavity of the plunger by means of a compressed metal spring, a guide tube and a shatter ring broken by adequate thumb compression, after the intended use of the complex assembly.

Pursuing the same goal, Gillespie in U.S. Pat. No. 5,180,370 (Jan. 19, 1993) described a syringe having an internal mechanism for retracting the needle into a hollow plunger after use. In one embodiment, the needle is manually retracted by pulling back on a vented hollow plunger after a plug is inserted into the leading end of the syringe. In a second embodiment, the needle is propelled by a compressed spring tripped by manipulation to confine the needle within the plunger. Owing to the complexity of sliding and springing internal pans, along with three integral breakable components cited in this patent, it is uncertain that the concept will prove useful in current medical practice.

None of the prior art cited teaches the use of a disposable syringe or medication-filled cartridge having leading inside slip and threaded connections for temporarily holding the trailing hub of a hollow-bore steel needle; or the use of a breakable plunger for retracting said hollow-bore steel needle into a safe position into the bore of said syringe or cartridge, instead of into a hollow piston confined within the bore. Therefore, I submit the following modifications of the foregoing prior art in terms which might prove practical currently.

DEFINITIONS

Syringes vs. Cartridges

Webster's Dictionary defines a syringe as "a piston-fitted hand cylinder, or a rubber bulb with a nozzle into which a fluid is sucked and then ejected in a stream for cleansing, spraying or injecting".

Webster's Dictionary defines a cartridge as "a cased explosive charge, also containing the missile when made for rifles or shotguns; alternatively, as a holder for a roll of film or ink refill for a fountain pen".

Dorland's Medical Dictionary defines a syringe as "an instrument for injecting liquids into or withdrawing them from any vessel or cavity. dental s., a small syringe into which is fitted a hermetically sealed cartridge which contains an anesthetic solution; used in operative dentistry. hypodermic s. a syringe, usually of small caliber, by means of which drugs in solution or other liquids are injected through a hollow needle of small bore into the subcutaneous tissues. Luer's s., Luer-Lok s., a glass syringe for intravenous or hypodermic use, with a metallic tip and locking device to hold the needle firmly in place.

In medical and dental practice, disposable syringes are customarily supplied devoid of fluid, but are supplied with trailing flanges and pistons activated by means of trailing plungers. In reusable glass syringes, now seldom used, the plungers and pistons usually consist of a one piece glass cylinder with a trailing flange. Alternatively, some reusable metal or plastic syringes are filled by disposable cartridges which are fluid-filled, but lack trailing flanges and plungers to activate contained pistons for expelling said fluid.

Because medical hypodermic syringes and cartridges are essentially hollow cylinders which differ in content, as well as appendages, they will be described as functionally separate entities herein.

Cylinders vs. Cylindroids

Webster's Dictionary defines a cylinder as "a solid figure traced out when a rectangle rotates using one of its sides as an axis of rotation; alternatively, a solid or hollow body having this form"; and a cylindroid as "a cylinder with elliptical right sections". Therefore, the term, cylindroid, will be used herein, when applied to the technical description of commonly used medical syringes and cartridges.

SUMMARY

Currently it is imperative to find better ways to prevent the person to person spread of AIDS, hepatitis and other blood-borne diseases by means of syringes, cartridges and needles commonly used for giving prescribed medical injections or shooting intravenous drugs. To this end, I describe a safely usable, non-reusable syringe and medicine cartridge with inside threads, an internally retractable needle and a breakable plunger, as described briefly in the abstract. Attractive features of this assembly are:

1. The assembly can be fabricated simply, efficiently and at minimal cost by manufacturers accustomed to the extrusion molding of syringes or medication cartridges, along with standard fitting hollow-bore steel needles, hubs, pistons and plungers. Actually, the number of parts is the same, but are rearranged such that the needle is easily retracted into a hollow puncture-resistant cylinder by the plunger after use.
2. The assembly is not friendly to intravenous drug users because:
   a. After proper use by medical or dental health care workers, it is impractical to refill the syringe or a spent cartridge, because the needle is confined inside and the plunger is broken off.
   b. Even if the plunger is reconstituted, it will be very difficult to prevent leakage from the leading end of the syringe or cartridge without fitting equipment used by the manufacturer to seat the needle within the leading end of the syringe or cartridge before use.
3. The assembly is very friendly to health care workers because:
   a. During use, the syringe assembly is manipulated like any standard syringe with a Luer-Lok attached needle. Because the needle is pre-seated and locked inside, the user does not attach the needle. Presumably, the licensed manufacturer will supply a variety of choices among commonly used needle lengths and bores.
   b. During use the cartridge assembly, after screwing on the plunger, is used like any loaded syringe with a Luer-Lok attached needle. Because the needle is already attached inside and the cartridge is pre-filled, the user does not waste time arming and filling the assembly. Manufacturers should supply choices of solutions and needles.
   c. After use for giving an intended measured injection into a patient, proper twisting and retraction of the syringe or cartridge plunger will pull the hollow-bore steel needle into puncture-resistant confines of the syringe or cartridge, such that the needle is not exposed during exit from the patient. However, if the needle is pulled out of the patient before being fully retracted into the syringe or cartridge, the user can continue the process of twisting and retracting the plunger employing both hands in safe positions far from the projected thrust of an exposed needle. Once the needle is fully retracted and the trailing end of the plunger is broken off, the confined needle and used syringe or cartridge can be disposed safely, compactly and conveniently.
4. This assembly in syringe and in cartridge form is manufacturer- and user-friendly, as well as time-, cost- and bulk-efficient.

DESCRIPTION OF THE PREFERRED EMBODIMENTS

Figure 1:
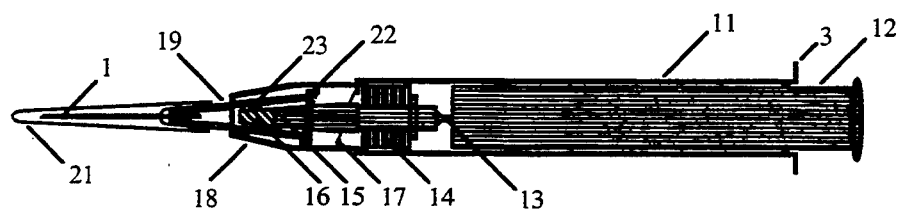
FIG. 1 is a diagrammatic axial section of an empty hollow cylindroid, embodied as syringe with a disposable sterile sheath covering the exposed part of the needle. (Scale 1:1)

A first preferred embodiment of a safely useful, non-reusable cylindroid syringe is shown in FIGS. 1-5. In FIG. 1 a syringe (11) is shown activated by an inserted plunger (12) having a breakable mid-portion (13), a surrounding hollow elastomeric piston (14) and a tapered leading end (15) which terminates in right handed threads (16). The syringe (11) contains an internal left hand threaded Luer-Lok (17) near the leading end which tapers (18) to form a slip connection over the conical hub (19) of a hollow-bore steel needle (1) whose exposed leading end is covered by a disposable needle sheath (21) which slip connects to the leading exposed portion of the conical needle hub (18). The mid-portion of the conical needle hub (19) slips into the leading tapered portion of the syringe (18) until it binds to constitute a water-proof seal. The trailing portion of the conical needle hub (19) embodies a an external flange (22) which engages the internal left hand threaded Luer-Lok (17) inside the leading end of the syringe (11) to tighten the water-proof seal, as well as immobilize the conical needle hub (19) within the tapered leading end (18) of the syringe (11). The internal surface of the conical needle hub (19) is right hand threaded (23) to matingly engage with the threads (16) on the leading tapered end (15) of the syringe plunger (12).

Secure and water-tight assembly of parts 14-23 in the leading end of the syringe (11) is predicated on establishment of an impaction of the external surface of the conical needle hub (19) into the leading tapered portion (18) of the syringe. Such an impaction will be created when the external flange (22) on the trailing end of the conical needle hub (19) is rotated counter-clockwise until stopped by friction inside Luer-Lok (17) in the leading end of the syringe (11) and by friction between the cone of the needle hub (19) and the taper (18) in the leading end of the syringe (11). Paired slots in the perigee of the trailing flange (22) of the conical needle hub (19) shown at (43) in FIGS. 4-5 will facilitate such counter-clockwise rotation by means of a fitting screw driver inserted into the trailing end of the syringe (11) before the plunger (12) is inserted. Later, when the plunger (12) is inserted into the syringe (11), it is preferable to not engage or fully engage the right handed threads (16) on the leading end of the syringe plunger (12), so that this activating plunger will be free to move backward in the syringe (11).

Figure 2:
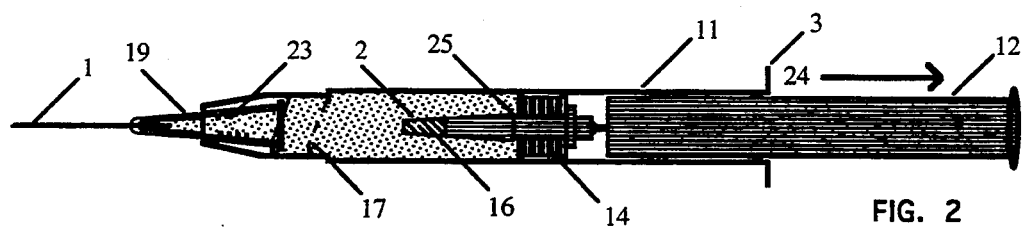
FIG. 2 is a diagrammatic axial section of said cylindroid syringe during filling.

As shown in FIG. 2, the needle sheath (21) has been discarded. When the syringe plunger (12) is manually retracted within the syringe (11) in the direction of the arrow (24), the syringe can be filled with fluid (2) through an immersed needle (1) by means of suction created by the hollow elastomeric piston (14) which is prevented from sliding forward over the syringe plunger (12) by an expanded segment (25).

Figure 3:
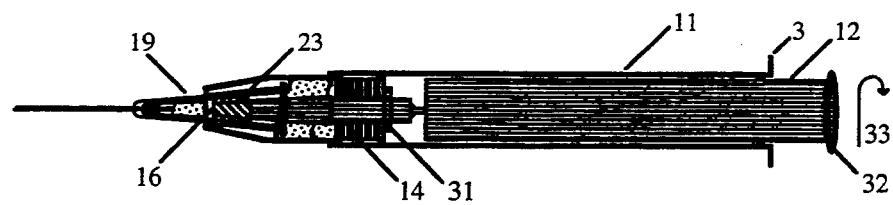
FIG. 3 is a diagrammatic axial section of the same after emptying and engagement of the leading threaded plunger end into mating threads in the needle hub.

As shown in FIG. 3, after the liquid contents of the syringe (11) have been expelled by pushing forward on the plunger (12) which activates the hollow elastomeric syringe piston (14) and prevents backward piston displacement by means of a circular flange (31), clockwise rotation of the trailing flange (32) of the plunger (12) in the direction of the arrow (33) will cause the right handed threads (16) on the leading portion of the syringe plunger (12) to matingly engage the right handed threads (23) inside the conical needle hub (19).

Figure 4:
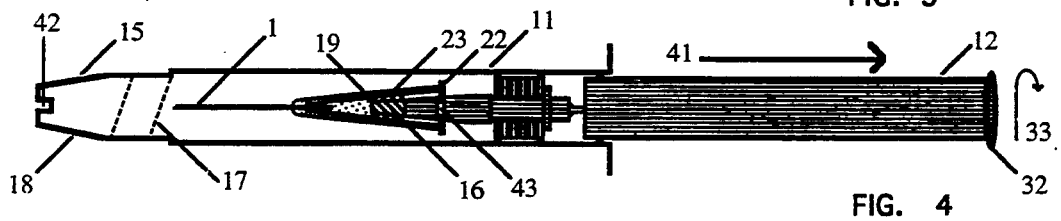
FIG. 4 is a diagrammatic axial section rotated 90°, showing the empty cylindroid syringe after the needle hub has been fully retracted by means of the syringe plunger.

As shown in FIG. 4, after the right handed threads (16) on the leading portion of the syringe plunger (12) are matingly engaged with the right handed threads (23) inside the conical needle hub (19), continued clockwise rotation of the trailing flange (32) of the syringe plunger (12) in the direction of the arrow (33), coupled with retraction of the syringe plunger (12) in the direction of the arrow (41), will disengage the trailing flange (22) on the conical needle hub (19) from the internal left-handed threaded Luer-Lok (17) and disengage the leading conical portion of the needle hub (19) from its frictional connection with the inside taper (18) on the leading end of the syringe (11). As results, the hollow-bore steel needle (20) will be retracted by means of its conical hub (19) into the confines of syringe (11). Paired vents (42) in the leading taper (18) of the syringe (11) will permit the emptied syringe to suck air and prevent the creation of a vacuum, in the event that the leading end of the syringe is pressed directly against a patient's skin during withdrawal of the needle (1). Such paired vents (42), as well as paired slots (43), in the perigee of the trailing flange (22) of the conical needle hub (19) are not shown in FIGS. 1–3 because the axis of the syringe is rotated 90° in FIGS. 4–5.

Figure 5:
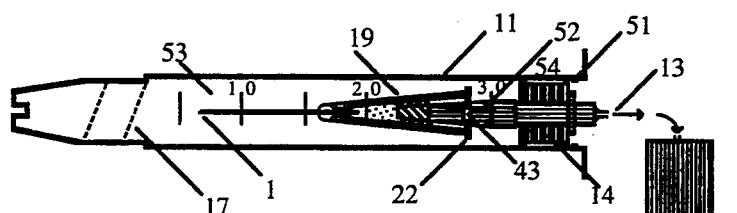
FIG. 5 is a diagrammatic axial section, also rotated 90°, showing the empty cylindroid syringe after the trailing end of the plunger has been broken away from the leading end to leave the needle held by the piston in the confines of the syringe.

As shown in FIG. 5, complete retraction of the plunger (12) from the syringe (11) through the open trailing end is stopped by a circular constricting flange (51) in the syringe bore which impedes extraction of the trailing flange (54) of the hollow elastomeric piston (14). Stoppage of the trailing flange (54) of the piston (14), as well as insertion of the piston (14) during assembly, will be enhanced by making the internal circular trailing flange (51) in the trailing bore of the syringe (11) like a wedge whose broad base is oriented toward the leading bore of the syringe (11). Thus, the hollow elastomeric piston (14) will be easy to insert, but hard to extract from the trailing bore an empty syringe (11) or an empty cartridge (61), as described later.

With stoppage of the piston (14) at the circular internal flange (51), the trailing portion of the syringe plunger (12) is broken away from the leading portion at the breakable midpoint (13) to leave the trailing portion (12) separate, and the leading portion (52) confined in the syringe, along with the stopped hollow elastomeric plunger (14) through which the remaining portion of the syringe plunger (52) passes to retract the hollow-bore steel needle (20) by means of its conical hub (19). Consequently, the needle (1) is safely confined within the bore of the emptied syringe (11) and the syringe/needle can not be reused, because the syringe plunger (12) is broken away and the conical needle hub (19) can not be reseated properly into the Luer-Lok (17) in the leading end of the syringe (11) without using the paired slots (43) in the perigee of the trailing needle hub flange (22) to screw this flange counter-clockwise into the left handed threads in the Luer-Lok (17).

Figure 6:
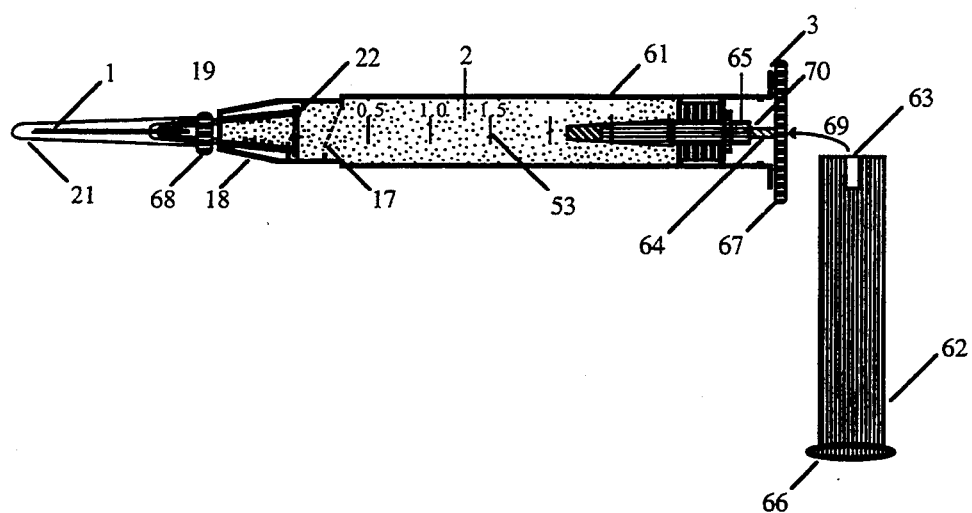
FIG. 6 is a diagrammatic axial section of a prefilled cylindroid cartridge with a disposable needle sheath covering the exposed part of the needle, an attachable cartridge plunger, and detachable hermetic seals at each end of the cartridge.

A first preferred embodiment of a non-reusable, safely disposable fluid filled (2) cylindroid medication cartridge is shown in FIGS. 6–9. FIG. 6 shows a filled cartridge (61) which is activated by a cartridge plunger (62) having a trailing part (62) whose leading end contains a threaded female receptacle (63) which releasably mates with a right hand threaded projection (64) on the trailing end of a leading part (65) when the trailing part of the plunger is rotated clockwise by means of a trailing flange (66). The prefilled cartridge (61) is hermetically and sterile sealed at its open trailing end by a detachable flat tab (67); and sealed similarly at its leading end by a detachable circular tab (68) which overlies a slip connection between a disposable needle sheath (21) and the leading end of a conical needle hub (19) which stabilizes the leading hollow-bore steel needle (1). The conical needle hub (19), in turn, is stabilized within the leading end of the end of the cartridge (61) by means of its trailing flange (22) rotated counter-clockwise into a Luer-Lok (17) inside the leading end of the cartridge (61), as well as by the leading tapered end (18) of the cartridge (61) wherein the conical needle hub (19) becomes impacted during assembly, precisely as described with respect to the safe disposable syringe (11) shown in FIGS. 1–5.

Preparation of the fluid filled (2) cartridge (61) just prior to intended use is accomplished by sequentially removing the trailing detachable flat tab (67) which covers the open trailing end of the cartridge (61); engaging the threaded female receptacle (63) on the trailing part of the cartridge plunger (62) which releasably mates with a right hand threaded projection (64) on the trailing end of the leading part (65) when the trailing pan of the plunger is rotated clockwise by means of the trailing flange (66); and doing so in the direction of the arrow labeled (69). Next to last, the detachable circular tab (68) should be removed; and, last, the disposable needle sheath (21).

Figure 7:
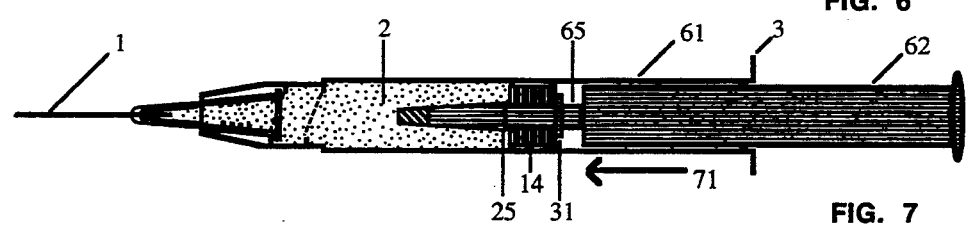
FIG. 7 is a diagrammatic axial section of the cylindroid cartridge partly emptied by means of the attached cartridge plunger and hollow piston securely held by the plunger.

As shown in FIG. 7, after the disposable needle sheath (21) is removed, and the trailing part of the of the cartridge plunger (62) is clockwise mated with the leading part (65) by means of the right hand threading mechanisms shown at 63,64,69 in FIG. 6, the filled cartridge (61) showing apparent connection between mating plunger parts (63–64) is useful for injecting fluid medication with forward displacement of the plunger (62), as indicated by the arrow (71).

Figure 8:
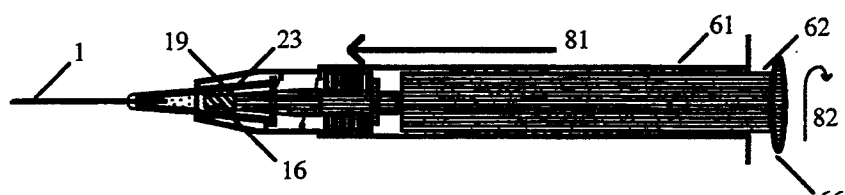
FIG. 8 is a diagrammatic axial section rotated 90°, showing the emptied cylindroid cartridge after the leading threaded end of the cartridge plunger has been rotated to the fight to engage mating threads inside the needle hub.

As shown in FIG. 8 by the elongated arrow (81), maximal forward displacement of the cartridge plunger (62) empties the cartridge (61) and inserts the leading right hand threaded end (16) of the plunger (62) into receptive threads (23) inside the conical hub (19) which holds the leading hollow-bore steel needle (1). Then, clockwise rotation of the trailing flange (66) of the cartridge plunger (62) in the direction of the arrow (82) seats the leading threads (16) of the cartridge plunger (62) into mating threads (23) inside the conical needle hub (19).

Figure 9:
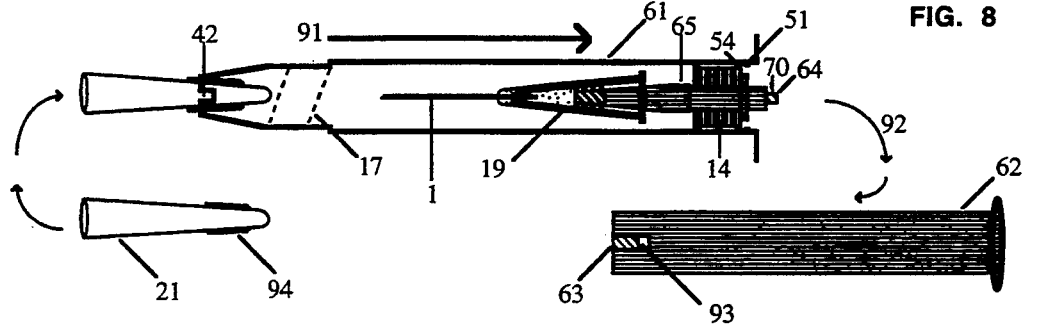
FIG. 9 is a diagrammatic axial section, also rotated 90°, showing the emptied cylindroid cartridge after the leading end of cartridge plunger has been broken away from the trailing end to leave the needle held by the hollow piston in the confines of the cartridge.

Finally, as indicated by the long arrow (91) in FIG. 9, retraction of the cartridge plunger (62) pulls the leading part of the plunger (65) back to a point where the trailing flange (54) on the hollow elastomeric piston (14) is stopped by a circular constricting flange (51) in the trailing bore of the empty cartridge (61). With the piston (14) stopped, sharp downward angulation of the trailing part of the cartridge plunger (62) in the direction of the arrow (92) will cause the right hand threaded projection (64) on the leading part of the cartridge plunger (65) to break off, leaving the broken end (93) within the female threaded receptacle (63). Consequently, the needle (1) is safely confined within the bore of the emptied cartridge (61) and the cartridge/needle can not be reused, because the cartridge plunger (62) is broken away. Moreover, the conical needle hub (19) can not be reseated easily into the Luer-Lok (17) in the leading end of the cartridge (61), as already described with respect to a syringe (11), as shown in FIG. 5.

Usage of the first preferred embodiment of the syringe (11), as well as the first preferred embodiment of the prefilled cartridge (61) is simple. The user employs the syringe (11) or the cartridge (61) for injecting fluid medication, just as he/she would do customarily. However, after use for the intended purpose, he/she can rotate the trailing flange (32 or 66) of the syringe (12) or cartridge plunger (62) clockwise to engage the conical hub (19) of the leading hollow-bore steel needle; and then retract the plunger (12 or 62) until the surrounding hollow elastomeric piston (14) is stopped by a constricting flange (51) in the trailing end of an emptied syringe (11) or cartridge (61). Breakage of the plunger (12 or 62) leaves the leading hollow bore steel needle (1) safely confined inside the syringe (11) or cartridge (62) as shown. Moreover, the syringe (11) or cartridge (61) can not be reused because the plunger (12,62) is broken, and the retracted conical needle hub (19) would be difficult to reseat properly in the leading end of the syringe (11) or the empty cartridge (61) without a screw driver fitting the internal cone and paired slots (43) in the perigee of the trailing flange (22) on the conical needle hub (19).

It should be added that, in a second preferred embodiment of the cartridge version of the instant invention, the user need not break off the threaded portion (64) of the cartridge plunger (62) from leading part (65). Instead, he/she has the option to unscrew the trailing part of the plunger (62) from the leading part (65), such that a chosen plunger can be reused with another prefilled cartridge, as shown in FIG. 6. This embodiment has the advantage that a reliable inset female receptacle (63) for protruding male threads (64) on the leading part of the plunger (65) can be made of molded metal, instead of plastic material. As results, the screw-on and screw-off mechanisms might prove smoother, especially if the semi-trailing end of the trailing protrusion on the leading plunger part is provided with a flange (70) to control the depth of threading of mating parts (63-64), such that more leverage can be applied to assure subsequent plunger breakage or smoother operation of metal mating with matching plastic parts. However, the user is obliged to safely retain a reusable plunger to prevent subsequent use by others intending to use a spent cartridge with a functional plunger like a syringe for aspirating and injecting fluid medications under illicit circumstances.

As another desirable feature shown in FIG. 9, the disposable needle sheath (21) originally supplied before use of the syringe (11) or cartridge (61) can be made with an expanded portion near the leading end (94), so that reinsertion of this sheath closed end first into the leading end of the cartridge (61) or syringe (not shown) will prevent fluid leakage, as well as accidental forward movement of the retracted hollow-bore steel (1) through the leading end of the cartridge (61), after the cartridge or syringe is emptied.

Filling of the syringe (11) by the user presents no unusual problems, because the device is made to function like any other standard disposable syringe provided with a leading hollow-bore steel needle attached by means of its trailing hub to a Luer-Lok on the leading end of a syringe containing a functional piston. However, fluid filling of the cartridge (61) during fabrication presents problems to the manufacturer which can be solved by using a machine-tooled device whose leading end functions temporarily like that in the trailing portion of the plunger (62) to activate leading portion of the plunger (65) securely holding the piston (14) previously inserted into bore of the cartridge (61). After filling with a desired volume of fluid through the bore of the leading needle (1), the temporary device can be extracted, following which the trailing seal (67) and leading seal (68) can be applied and dispensed, along with the trailing portion of the plunger (62) having a fitting receptacle (63) for the threaded projection (64) on the trailing portion of the leading part of the plunger (65). Alternatively, the cartridge assembly can be fabricated in a submerged condition with the fluid intended for dispensation, after which the seals (67 & 68) can be applied. Subsequently, when the separate trailing portion of the plunger (61) is screwed onto the leading portion (65), the user will be supplied with a device which functions like a syringe.

Finally, it is essential that the syringe (11) and that the casing of the medication-filled cartridge be puncture-resistant and made of transparent material clearly labeled with respect to fluid volumes contained. Therefore, a clearly visible, gradated volume scale (53) beyond the leading end of the piston (14) is included in the syringe (11) and in the cartridge (61). In the case of the syringe (11), as shown in FIG. 5, the gradated volume scale (53) will permit the user to aspirate, by means of the solid plunger (12), the precise dose of fluid medication to be administered. In the case of the pre-filled cartridge (62), as shown reversed in FIGS. 6, the gradated volume scale (53) will permit the user to pre-discharge a chosen fluid medication in excess of a determined total dose. When correctly calculated doses of fluid medication are withdrawn by the piston (14) in the syringe (11), or discharged before ejection from a pre-filled cartridge (61), the user will find that the conical hub (19) and trailing flange (22) of the insertive hollow-bore steel needle (1) will mesh with corresponding receptive counterparts (19-18) and (22-17). In the case of correct meshing after injecting a desired fluid volume, the user will be delighted to find that the sharp leading tip of an insertive hollow-bore steel needle (1) is never exposed outside of the recipient's body during retraction, especially when adequate side-venting (42) of the leading cone of the syringe (11) or cartridge (61) permits unimpeded retraction of a hollow elastomeric piston (14) securely attached to a solid syringe plunger (12) or a two part cartridge plunger (62) to a predicted point of piston stoppage (51).

Alternatively, if the fluid dosages were calculated in excess with respect to a given patient's needs, the user retains the option of externally discharging the excess residuals conveniently into an appropriately placed safe receptacle in order to assure the already described meshing of all component syringe (11) or prefilled cartridge parts (61). Under such circumstances, the user may then safely retract the entire hollow-bore steel needle (20), along with its sustaining conical hub (19) into the puncture-resistant confines of said syringe (11) or cartridge (61), using both hands operating in positions far behind the longitudinal thrust of the sharp leading tip of the insertive hollow-bore steel needle (1).

Although this invention has been described with respect to preferred embodiments, it should be understood by those skilled in the art that additions, modifications, substitutions, deletions and other changes can be made. It will be understood that the details cited here are illustrative and not, necessarily, limiting.

Therefore, what I claim is:

1. A safely disposable, non-reusable device for aspirating, holding and injecting containable fluid medications, said device comprising in combination:
   (a) a leading hollow-bore steel needle with a conical needle hub; and
   (b) a detachable puncture-resistant conical needle cap which slip connects to form an air- and water-tight connection over said conical hollow needle hub and, when reversed, further comprises a plug for a leading end of said device; and
   (c) a hollow cylindroid consisting of three portions:
      (i) a leading conical portion with leading slot-like vents, an internal cone which slip connects over said conical needle hub and with internal left-handed threads matching with flanges on a trailing end of said conical needle hub to form a reversible inside Luer-Lok connection,
      (ii) a cylindric mid-portion housing an elastomeric piston suitable for aspirating or propelling said containable fluid medications when activated by a plunger,
      (iii) a cylindric trailing portion having an inside narrow annular flange, followed caudally by an outside wide annular flange; and
   (d) a finger-activated plunger having:
      (i) a leading end with right-handed threads,
      (ii) a mid-portion which passes through said elastomeric piston and has holding flanges leading and trailing said elastomeric piston, and
      (iii) a trailing end with leading means for reversibly engaging said mid-portion of said finger-activated plunger and an expanded trailing means for finger placement;
   and wherein said conical needle hub has means for releasably engaging said fight-handed threads on said leading end of said finger-activated plunger.

2. The device, as in claim 1, wherein said hollow cylindroid is supplied without said containable fluid medications and with a breakable portion in said trailing end of said finger-activated plunger.

3. The device, as in claim 1, wherein said hollow cylindroid is supplied filled with said containable fluid medications and with said finger-activated plunger having said trailing end reversibly attachable to a trailing receptacle in said mid-portion by means of right-handed threads.

4. The device, as in claim 1, wherein a surface of said hollow cylindroid is marked to indicate the volume of said containable fluid medications actually contained before, during and after operation.

* * * * *